(12) United States Patent
Samani et al.

(10) Patent No.: US 7,682,813 B1
(45) Date of Patent: Mar. 23, 2010

(54) METHANE GENERATION FROM WASTE MATERIALS

(75) Inventors: Zohrab A. Samani, Las Cruces, NM (US); Adrian T. Hanson, Las Cruces, NM (US); Maritza Macias-Corral, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 90 days.

(21) Appl. No.: 11/373,739

(22) Filed: Mar. 9, 2006

Related U.S. Application Data

(60) Provisional application No. 60/661,180, filed on Mar. 10, 2005.

(51) Int. Cl.
*C12P 5/02* (2006.01)
*C12M 1/00* (2006.01)
*C12M 1/10* (2006.01)
*C12M 1/02* (2006.01)

(52) U.S. Cl. .............. 435/167; 435/290.1; 435/290.2; 435/290.3; 435/290.4

(58) Field of Classification Search ............... 435/167, 435/290.1, 290.4
See application file for complete search history.

(56) References Cited

U.S. PATENT DOCUMENTS

| | | | | |
|---|---|---|---|---|
| 2,113,443 A | * | 4/1938 | Eggerss | 24/20 R |
| 2,703,248 A | * | 3/1955 | Mauer | 292/256.65 |
| 4,274,838 A | * | 6/1981 | Dale et al. | 48/111 |
| 4,323,367 A | | 4/1982 | Ghosh | |
| 4,351,729 A | * | 9/1982 | Witt | 210/603 |
| 4,396,402 A | | 8/1983 | Ghosh | |
| 4,503,154 A | * | 3/1985 | Paton | 435/167 |
| 5,269,634 A | * | 12/1993 | Chynoweth et al. | 405/303 |
| 5,447,850 A | * | 9/1995 | McCann | 435/42 |
| 6,299,774 B1 | | 10/2001 | Ainsworth et al. | |
| 6,783,677 B1 | * | 8/2004 | Irani | 210/603 |
| 2004/0099599 A1 | * | 5/2004 | Van Vliet et al. | 210/603 |

OTHER PUBLICATIONS

"Characterization of Municipal Solid Waste", www.fal.com, Web Page for Franklin Associates. Ltd., (Mar. 1996).
Bae, J. H., et al., "Effects of Leachate Recycle and Anaerobic Digester Sludge Recycle on the Methane Production from Solid Wastes", *Wat. Sci. Tech.*, vol. 38, No. 2, Elsevier Science, Ltd., Great Britain,(1998),169-168.
Barlaz, Morton A., et al., "Methane Production from Municipal Refuse. A Review of Enhancement Techniques and Microbial Dynamics", *Critical Reviews in Environmental Control*, vol. 19, Issue 6,(1990),557-584.
Brummeler, E. T., et al., "Dry Anaerobic Batch Digestion of the Organic Fraction of Municipal Solid Waste", *J. Chem. Tech. Biotechnol.*, vol. 50, SCI, Great Britain,(1991),191-209.

(Continued)

*Primary Examiner*—Walter D Griffen
*Assistant Examiner*—Lydia Edwards
(74) *Attorney, Agent, or Firm*—Vidal A. Oaxaca; Deborah A. Peacock; Peacock Myers, P.C.

(57) ABSTRACT

An organic solid waste digester for producing methane from solid waste, the digester comprising a reactor vessel for holding solid waste, a sprinkler system for distributing water, bacteria, and nutrients over and through the solid waste, and a drainage system for capturing leachate that is then recirculated through the sprinkler system.

13 Claims, 2 Drawing Sheets

OTHER PUBLICATIONS

Brummeler, E. T., et al., "Dry Anaerobic Digestion of Solid Organic Waste in a Biocel Reactor at Pilot-Plant Scale", *Wat. Sci. Tech.*, vol. 25, No. 7, IAWPRC, Great Britain,(1992),301-310.

Chynoweth, D. P., et al., "A Novel Process for Anaerobic Composting of Municipal Solid Waste", *Applied Biochemistry and Biotechnoloöy*, vol. 28/29, The Humana Press, Inc.,(1991),421-432.

Forstner, U., *Integrated Pollution Control*, 1st ed., Springer-Verlag Berlin Heidelberg,(1998),130-140.

Ghosh, Sambhunath, et al., "Anaerobic acidogenesis of wastewater sludge", *Journal WPCF*, vol. 47, No. 1,(Jan. 1975),30-45.

Ghosh, S., et al., "Biogasification of Solid Wastes by Two-Phase Anaerobic Fermentation", *Proceedings of the Third Biomass Conference of the Americas*, (1997),1193-1204.

Ghosh, Sambhuanth, "Improved Sludge Gasification by Two-Phase Anaerobic Digestion", *Journal of Environmental Engineering*, vol. 113, No. 6, ASCE,(Dec. 1987),1265-1284.

Ghosh, Sam, "Pilot-Scale Demonstration of Two-Phase Anaerobic Digestion of Activated Sludge", *Wat. Sci. Tech.*, Vo. 23, Kyoto, IAWPRC, Great Britain,(1991),1179-1188.

Ghosh, Sambhunath, "Role of Anaerobic Digestion in Alleviating Environmental Problems in the United States", *J. of Hudrau., Coast. and Environ. Eng.*, No. 521, No. 8,(1995),239-248.

Ince, O., "Performance of a Two-Phase Anaerobic Digestion System When Treating Dairy Wastewater" *Wat. Res.*, vol. 32, No. 9, Elesevier Science, Ltd., Great Britain,(1998),2707-2713.

Leckie, James O., et al., "Landfill Management with Moisture Control", *Journal of the Environmental Engineering Division, Proceedings of the American Society Of Civil Engineers*, vol. 105, No. EE2,(Apr. 1979),337-355.

Mata-Alvarez, Joan, "A Dynamic Simulation of a Two-Phase Anaerobic Digestion System for Solid Wastes", *Biotechnology and Bioengineering*, vol. 30, John Wiley & Sons, Inc.,(1987),844-851.

Mata-Alvarez, Joan, et al., "Anaerobic Digestion of the Barcelona Central Food Market Organic Wastes: Experimental Study", *Bioresource Technology*, vol. 39,(1992),39-48.

McCarty, Perry L., "Anaerobic Waste Treatment Fundamentals, Part Four, Process Design", *Public Works*, vol. 92, No. 12,(Dec. 1964),95-99.

McCarty, Perry L., "Anaerobic Waste Treatment Fundamentals, Part One, Chemistry and Microbiology", *Public Works*, vol. 95, No. 9,(Sep. 1964),107-112.

McCarty, Perry L., "Anaerobic Waste Treatment Fundamentals, Part Three, Toxic Materials and Their Control", *Public Works*, vol. 92, No. 11,(Nov. 1964),91-94.

McCarty, Perry L., "Anaerobic Waste Treatment Fundamentals, Part Two, Environmental Requirements and Control", *Public Works*, vol. 92, No. 10,(Oct. 1964),123-126.

O'Keefe, D. M., et al., "Sequential Batch Anaerobic Composting of Municipal Sold Waste (MSW) and Yard Waste", *Wat. Sci. Tech.*, vol. 27, No. 2, LAWQ, Great Britain,(1993),77-86.

Oleszkiewicz, Jan A., et al., "High-Solids Anaerobic Digestion of Mixed Municipal and Industrial Waste", *Journal of Environmental Engineering*, vol. 123, No. 11, ASCE,(Nov. 1997),1087-1092.

Owens, J. M., et al., "Biochemical Methane Potential of Municipal Solid Waste (MSW) Components", *Wat. Sci. Tech.*, vol. 27, No. 2, IAWQ, Great Britain,(1993),1014.

Pavan, P., et al., "Thermophilic Semi-Dry Anaerobic Digestion Process of the Organic Fraction of Municipal Solid Waste During Transient Conditions", *Environmental Technology*, vol. 15, Selper, Ltd., (1994), 1173-1182.

Pohland, Frederick G., "Accelerated Solid Waste Stabilization and Leachate Treatment by Leachate Recycle Through Sanitary Landfills", *Progress In Water Technology*, vol. 7, Nos. 3/4, Pergamon Press, Great Britain,(1975),753-765.

Pohland, F. G., et al., "Developments in Anaerobic Treatment Processes", *Biotechnol. & Bioeng., Symp. No. 2*, John Wiley & Sons, Inc.,(1971),85-106.

Rikitala, Jukka A., et al., "A Two-Stage Thermophilic Anaerobic Process for the Treatment of Source Sorted Household Solid Waste", *Biotechnology Letters*, vol. 16, No. 10,(Oct. 1994),1097-1102.

Samani, Z., et al., "Producing Energy from Municipal Solid Waste", *NEDO International Bio-Eneray Conference, Tokyo, Japan*, (Mar. 1998),1-22.

Sarapatka, Borivoj, "A Study of Biogas Production During Anaerobic Fermentation of Farmyard Manure", *Biomass and Bioenergy*, vol. 5, No. 5, Pergamon Press, Ltd., Great Britain,(1993),387-393.

Speece, R. E., *Anaerobic Biotechnology for Industrial Wastewaters*, Archae Press,(1996),93-94.

Strydom, J. P., et al., "Two-phase anaerobic digestion of three different dairy effluents using a hubrid bioreactor", *Water SA*, vol. 23, No. 2,(Apr. 1997),151-156.

Townsend, T. G., et al., "Acceleration of Landfill Stabilization Using Leachate Recycle", *Journal of Environmental Engineering*, vol. 122, No. 4, ASCE,(Apr. 1996),263-268.

Vieitez, E. R., et al., "Kinetics of accelerated solid-state fermentation of organic-rich municipal solid waste", *Water Science and Technology*. Vo. 41, No. 3, IWA Publishing,(2000),231-238.

Wolff, J., et al., "Anaerobni Fermentace Schlevske Mrvy a Vlivy Pusobici Na Produkci Bioplynu", *Zemedelska Technika (some translation provided)*, vol. 34,(1988),165-171.

Zhang, Tian C., et al., "Comparison of One-Phase and Two-Phase Anaerobic Digestion Processes in Characteristics of Substrate Degradation and Bacterial Population Levels", *Wat. Sci. Tech.*, vol. 23, Koyoto, JAWPRC, Great Britain,(1991),1157-1166.

Beccari, M. et al., "Two-Reactor System with Partial Phase Separation for Anaerobic Treatment of Olive Oil Mill Effluents", *Wat. Sci. Tech.* vol. 38, No. 4-5, Elsevier Sciences Ltd., Great Britain 1998, 53-60.

Chynoweth, D. P. et al., "Sequential Batch Anaerobic Composting of the Organic Fraction of Municipal Sold Waste", *Wat. Sci. Tech.* vol. 25, No. 7, IAWPRC, Great Britain 1992, 327-329.

De Baere, L. et al., "Anaerobic Fermentation of Refuse", *Resources and Conservation* vol. 14, Elsevier Science Publishers B.V., Amsterdam, The Netherlands 1987, 295-308.

Kubler, Hans et al., "Three-Phase Anaerobic Digestion of Organic Wastes", *Wat. Sci. Tech*, vol. 30, No. 12, IAWQ, Great Britain 1994, 367-374.

Lay, Jiunn-Jyi et al., "Developments of Bacterial Population and Methanogenic Activity in a Laboratory-Scale Landfill Bioreactor", *Wat. Res.* vol. 32, No. 12, Elsevier Science Ltd. Great Britain 1998, 3673-3679.

Shin, H.-S. et al., "Anaerobic Digestion of Distillery Wastewater in a Two-Phase UASB System", *Wat. Sci. Tech.* vol. 25, No. 7, IAWPRC, Great Britain 1992, 361-371.

Yeoh, B. G. et al., "Two-Phase Anaerobic Treatment of Cane-Molasses Alcohol Stillage", *Wat. Sci. Tech.* vol. 36, No. 6-7, Elsevier Science Ltd., Great Britain 1997, 441-448.

* cited by examiner

METHANE GENERATION FROM WASTE MATERIALS

CROSS-REFERENCE TO RELATED APPLICATIONS

This application claims priority to the filing of U.S. Provisional Patent Application Ser. No. 60/661,180, titled "Improved Methane Generation from Waste Materials", filed on Mar. 10, 2005, and the specification of that application is incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. 2001-35501-10100 awarded by the U.S. Department of Agriculture/CSREES and Grant No. DE-FC04-AL6743 awarded by the U.S. Department of Energy.

BACKGROUND OF THE INVENTION

1. Field of the Invention (Technical Field):

The present invention relates to methods and apparatuses for the production of methane from waste material such as manure.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Millions of tons of solid wastes are generated each year from municipal, industrial, and agricultural sources. Also, the methane and carbon dioxide released from landfills is a major concern for global warming. There is a great deal of interest for alternative waste management techniques which can accelerate the anaerobic decomposition of the organic fraction of the solid waste.

There are various methods used for the stabilization of organic waste. These include composting, single phase anaerobic digestion, and two-phase anaerobic digestion. The composting causes quick decomposition but also results in uncontrolled release of carbon dioxide to the atmosphere without the potential benefit of capturing energy of the waste. In contrast, the single phase anaerobic digestion system can produce gas with 40-60 percent methane which can be put to beneficial use. However, in the traditional single phase anaerobic digestion system, the acid forming and methane forming bacteria exist in the same biological environment. In such an environment, the volatile fatty acids ("VFA's") production proceeds at a much faster rate than the rate of conversion of VFA's to methane. This may cause acids to accumulate, resulting in a pH drop, and a consequent inhibition of methanogenesis.

Two-phase anaerobic digestion systems have been designed to avert the imbalance between the processes of acidogenesis and methanogenesis. (Pohland, F. G. and Ghosh, S., "Developments In Anaerobic Treatment Process", *Biotechnol. and Bioeng.* 1971, 2, 85-106; U.S. Pat. No. 4,323, 367; U.S. Pat. No. 4,396,402). The imbalance was removed by physically isolating the two major microbial phases in two separate reactors.

A two-phase system consists of a solid phase reactor and methane phase reactor. In the solid phase, water is applied from the top of the waste using a drip or sprinkler irrigation system. The leachate is collected at the bottom of the solid phase using an under-drain sump, and the leachate is then re-circulated through the solid waste bed until a desired level of volatile fatty acids ("VFA's") is achieved in the leachate. At this point, the leachate is transferred to the methane production reactor where the VFA is converted to methane in a very short time (2-3 days). The overflow from the methane production reactor is then returned to the solid phase for recirculation through the solid waste bed to replenish the VFA concentration. The system works with a relatively small quantity of water (about 25% greater than the solid waste field capacity on weight basis) which is constantly re-circulated between solid phase and methane phase.

The two-phase system has several advantages over the traditional single phase systems. However, the two phase system is difficult to implement and costly to build. Therefore, its application has been limited.

Examples of other approaches include the use of tanks that are simply loaded with solid waste which is allowed to react with bacteria over time. (Wolff, J., and Appelfeldova, V., "Anaerobic fermentation of farmyard manure and the factors influencing biogas production", *Zemedelska Technica* 1988, 3, 165-171; Sarapatka, B., "A study of biogas production during anaerobic fermentation of farmyard manure", *Biomass and Bioenergy* 1993, 5, 387-393). However, such static containers suffer from mass transfer problems resulting from the presence of non-homogenous material and the lack of mixing, thus resulting in a low biogas yield. Also, the reactors described are heavy (metal) and large equipment is needed to remove the caps or covers of such reactors. The construction of such reactors is expensive.

Municipal solid wastes are major sources of air, water, and soil contamination. There is a need for alternative waste management techniques that are cost effective to better utilize the waste and minimize its adverse environmental impact.

SUMMARY OF THE INVENTION

The present invention provides a solid waste digester for generating methane. An embodiment of the solid waste digester comprises a reactor vessel within which solid waste is placed, the vessel comprising at least one upright side wall, a floor, and an entrance on a side of the vessel, a cover disposed over the vessel to seal the vessel, a sprinkler system disposed over the solid waste for distributing water, bacteria, and nutrients over the solid waste, and a drainage system disposed at a bottom of the vessel for collecting leachate comprising water and bacteria and for sending the leachate through the sprinkler system.

The digester preferably comprises a storage unit for receiving the leachate until the leachate is recirculated to the solid waste via the sprinkler system. The digester also preferably comprises a heating system disposed in the floor to heat the digester. The heating system preferably comprises a pipe having heated water therein.

The cover preferably comprises a flexible cover, and the drainage system preferably comprises a floor drain.

The solid waste preferably comprises a sloping configuration from a center of the vessel down to the wall(s) and the drainage system is disposed at the floor along the wall(s).

The cover is preferably sealed via a compression component. The entrance preferably comprises a reinforced, sealing liner and is preferably sealed via a water seal.

Another embodiment of the present invention comprises a method of methane generation comprising providing a digester comprising at least one upright wall and a floor defining a vessel, disposing a cover over the vessel to seal the vessel, providing an entrance to the vessel and disposing organic solid waste through the entrance into the vessel sprinkling water on the solid waste, providing acid producing bacteria to digest the solid waste and methane producing bacteria to convert the acids to biogas, draining a leachate from the floor, and recirculating the leachate to sprinkle the leachate over the solid waste.

The entrance preferably is preferably provided on a side of the vessel. The vessel is preferably heated.

A primary object of the present invention is to provide a cost effective system for the generation of methane from solid waste.

A primary advantage of the present invention is that it provides a higher biogas production and a shorter digestion period.

Another advantage of the present invention is that it provides for the use of lower weight components and eliminates the need for a separate gas storage tank. Also, the dimensions of the digester are not limited because the walls can be as long as needed so that there is practically no limit on the volume that may be constructed. The entrance to the reactor vessel makes loading and unloading of solid waste efficient and of lower cost.

Still another advantage of the present invention is that it provides for the use of practically unlimited volume.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
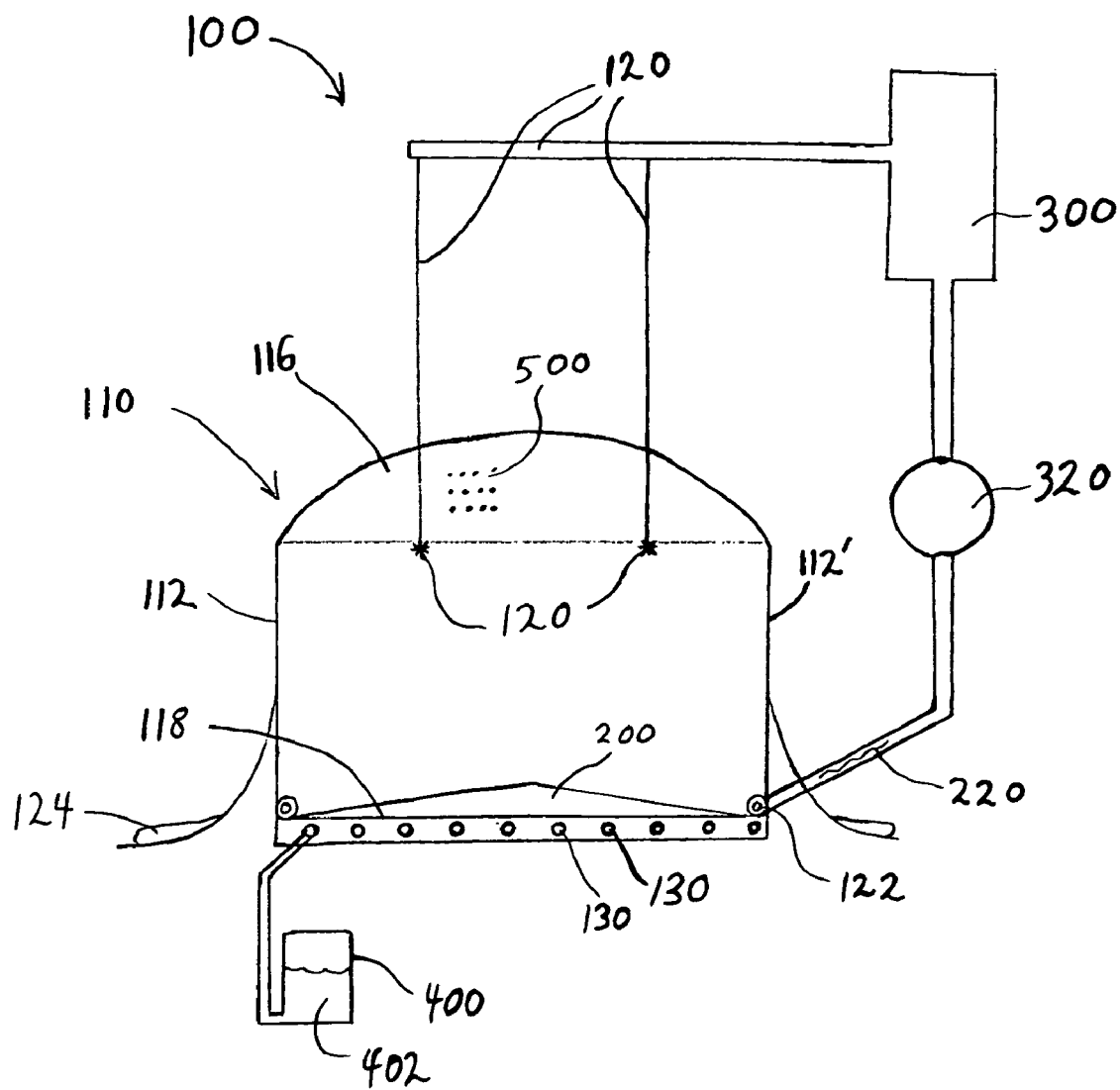
FIG. 1 is a schematic representation of a cross section of an embodiment of the digester of the present invention.

The present invention provides a system and method for the production of biogas, particularly comprising methane, that can be used as an energy source such as, for example, for the production of electricity. An embodiment of the present invention provides a single phase, self perpetuating dry digester using manure as a source of methane bacteria that is used for the anaerobic digestion of solid waste such as, but not limited to, feedlot or dry stable manure, a combination of dry and wet manure, or a combination of manure and other organic waste such as, for example, paper, cotton gin waste, food waste, etc. As used in the specification and claims herein, the terms "a", "an", and "the" mean one or more.

In a non-limiting embodiment of the present invention, organic solid waste such as food waste or other organic solid waste is placed into a digester comprising a vessel formed by at least one upright wall, a floor, and an entrance, preferably a side entrance. Preferably, the organic waste is placed in alternating layers with layers of manure. Fresh bovine manure is preferred as it has high levels of methane bacteria. Water is then added to the digester and re-circulated through the organic solid waste to spread the methane bacteria already presenting the manure to the remainder of the digester and solid waste. Acid producing bacteria convert the solid waste into volatile fatty acids. The methane bacteria convert the acids into biogas comprising methane, colonize the digester, and use the solid waste bed as a support media for attached growth. Thus, the digester has sufficient methane bacteria to consume acids that are generated as fast as those acids are produced by the acid producing bacteria. Therefore, the digester comprising a single reactor vessel accomplishes what a typical two-phase system accomplishes without the need for a second reactor vessel. The present invention provides an improvement over the prior art by reducing costs.

Thus, manure, or a combination of manure and other organic waste, is placed in a digester comprising a sealed vessel, and the digester is activated by adding water or water inoculated with methane enriched bacteria. The water is added to the digester via a sprinkler or drip system. A drainage system is placed at the bottom of the digester to collect the percolating water which is herein described as "leachate". The leachate is preferably collected in a storage unit before it is re-circulated periodically through the sprinkler system to maintain moisture and to distribute the methane bacteria within the organic solid waste material. In, for example, approximately 7-10 days, the methane bacteria naturally present in the manure (or that is provided via inoculated water) spreads through the digester and organic material and converts the digester into a self-perpetuating methane producing machine which, without further manipulation, produces methane gas. Water is then added occasionally to maintain the moisture in the digester. The digester operates for several days, such as, for example, approximately 30 to 50 days (depending on the type of organic material and method of inoculation) producing a biogas with, for example, approximately 55 to 65% methane. If inoculation is performed with the resident methane bacteria in the manure, the process takes approximately two weeks to reach full capacity. If the digester is inoculated with methane enriched leachate, the start up phase is faster (e.g., approximately 7-10 days).

The preferred design of the digester is such that manure or a mixture of manure and other organic waste is placed over a concrete pad. The concrete pad is heated by a heating system such as, but not limited to, a pipe or network of pipes circulating hot water. An irrigation system is used to apply leachate on the top of the organic waste pile. A drainage system in the concrete pad is used to collect the leachate. At least one wall forming a vessel is placed on the concrete pad, and the vessel is covered by a synthetic liner that is sealed by any means known in the art such as, but not limited to, a compression component. The liner is permanently sealed all about the vessel except from a side providing an entrance. The vessel can therefore be easily opened, vented, and loaded and reloaded as needed.

Figure 2:
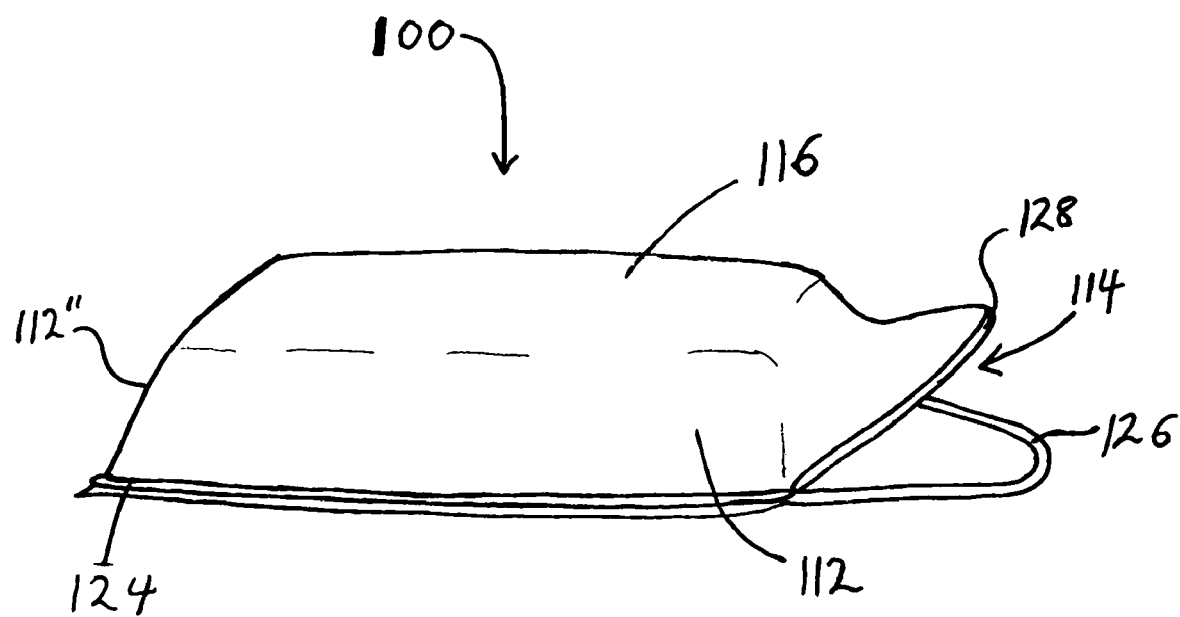
FIG. 2 is a top perspective view of the embodiment of FIG. 1.

Turning to FIGS. 1 and 2, which depict an embodiment that is illustrative, but not limiting, of the present invention, digester 100 is shown comprising reactor vessel 110. Reactor vessel 110 comprises three walls 112, 112', and 112", entrance 114, cover 116 disposed over walls 112, 112', and 112", and floor 118. Sealing/compression component 124 compresses cover 116 to provide a seal, preferably a permanent seal. Water seal 126 seals entrance 114. Brace or braces 128 are provided in entrance 114 to distribute force for effective sealing via water seal 126. Sprinkler system 120 is disposed within vessel 110 above solid waste 200. Solid waste 200 is placed in a configuration wherein it slopes from a center of vessel 110 down toward walls 112. Drainage system 122 collects leachate 220 which is sent to storage unit 300 for recirculation to sprinkler system 120 comprising a plurality of sprinkler nozzles. Heating pipes 130 are disposed in floor 118 to circulate hot water 402 and thus heat vessel 110. Hot water source 400 can be an electric generator that converts the generated methane to electricity. Pump 320 moves leachate to sprinkler system 120. Generated biogas 500 collects at the top end of vessel 110, under cover 116.

The present invention thus provides for rapid inoculation and startup of the digester which in turn results in higher biogas production and a shorter digestion period. The use of lighter materials for the cover not only provides for a lower weight in components but also provides a temporary gas storage area thus eliminating the need for a separate gas storage tank. Also, the dimensions of the digester are not limited because the walls can be as long as needed so that there is practically no limit on the volume that may be constructed and used. The entrance to the reactor vessel makes loading and unloading of solid waste efficient and relatively inexpensive.

EXAMPLE

A digester is constructed and used wherein the walls and floor of the reactor vessel comprise concrete, the cover comprises a flexible plastic liner, the entrance to the vessel comprises a reinforced (braced) flexible liner, the sprinkler system comprises PVC and sprinkler nozzles, the drainage system comprises PVC pipes, and the heating system comprises copper or steel pipes.

The startup phase of the reaction process takes approximately 7-10 days, and thereafter the digester becomes self-perpetuating for approximately 30 to 50 days and producing a biogas comprising approximately 55 to 65% methane.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated herein by reference.

What is claimed is:

1. A solid waste digester for generating methane comprising:
   a single phase reactor vessel horizontally disposable on a horizontal around surface within which solid waste is placed, said vessel comprising at least one upright side wall, a floor, and an easily openable entrance for loading, reloading, and unloading the solid waste comprising at least one brace for distributing force for sealing said easily openable entrance via a water seal disposed at said easily openable entrance;
   a cover comprising a liner disposed over said vessel and attached to said brace to seal said vessel;
   said entrance comprising said brace attached to a horizontal upper extension of said cover disposed above said entrance and said water seal attached to a horizontal lower floor extension disposed below said entrance;
   a sprinkler system disposed over the solid waste for distributing water, bacteria, and nutrients over the solid waste; and
   a drainage system disposed at a bottom of said vessel for collecting leachate comprising water and bacteria and for sending said leachate through said sprinkler system.

2. The digester of claim 1 further comprising a storage unit for receiving said leachate until said leachate is recirculated to said solid waste via said sprinkler system.

3. The digester of claim 1 further comprising a heating system disposed in said floor to heat said digester.

4. The digester of claim 1 wherein said cover comprises a flexible cover.

5. The digester of claim 1 wherein said drainage system comprises a floor drain.

6. The digester of claim 1 wherein said solid waste comprises a sloping configuration from a center of said vessel down to said at least one wall and wherein said drainage system is disposed at said floor along said at least one wall.

7. The digester of claim 3 wherein said heating system comprises a pipe having heated water therein.

8. The digester of claim 1 wherein biogas is accumulated within said vessel under said cover.

9. The digester of claim 1 further comprising a pad over which solid waste is placed.

10. The digester of claim 1 wherein said pad is a concrete pad.

11. The digester of claim 9 further comprising a heating system disposed in said pad.

12. The digester of claim 9 further comprising a drainage system disposed in said pad for collecting leachate.

13. The digester of claim 1 wherein said liner is sealed by a sealing compression component.

\* \* \* \* \*